United States Patent [19]

Finn

[11] Patent Number: 5,215,568
[45] Date of Patent: Jun. 1, 1993

[54] OXIME DERIVATIVES OF FORMYLPYRIDYL IMIDAZOLINONES, THE HERBICIDAL USE AND METHODS FOR THE PREPARATION THEREOF

[75] Inventor: John M. Finn, Mercerville, N.J.

[73] Assignee: American Cyanamid Company, Stamford, Conn.

[21] Appl. No.: 786,159

[22] Filed: Oct. 31, 1991

[51] Int. Cl.$^5$ .................. A01N 43/50; C07D 213/80
[52] U.S. Cl. ................... 504/253; 546/278; 504/193
[58] Field of Search .................. 546/278; 71/92

[56] References Cited

U.S. PATENT DOCUMENTS

| 4,237,123 | 12/1980 | Roman | 424/200 |
| 4,584,318 | 4/1986 | Peake et al. | 514/546 |
| 4,798,619 | 1/1989 | Los | 71/66 |
| 5,026,859 | 6/1991 | Finn | 546/268 |
| 5,039,333 | 8/1991 | Finn | 71/92 |

FOREIGN PATENT DOCUMENTS

| 0322616 | 7/1989 | European Pat. Off. | 546/268 |
| 62-174069 | 7/1987 | Japan | 546/268 |

OTHER PUBLICATIONS

Sandler and Karo, "Organic Functional Group Preparations III," Chapters 10 and 11 (Academic Press, New York 1973).
Takasugi et al., J. Antibiotics, 36:846 (1983).
Grochowski and Jurczak, Synthesis 682 (1976).
McKay et al., Candian J. Chem., 38:343 (1960).

Primary Examiner—C. Warren Ivy
Assistant Examiner—Zinna N. Davis
Attorney, Agent, or Firm—Peggy A. Climenson

[57] ABSTRACT

This disclosure describes new 5-oximio-2-(2-imidazolin-2-yl) pyridines having the following structure:

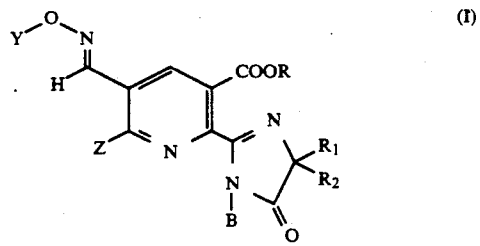

wherein Y is hydrogen, $C_1$-$C_4$ branched or unbranched alkyl optionally substituted with $C_{1}$-$C_4$ alkoxy, $C_{1}$-$C_4$ alkylthiol, halogen, $CO_2R_4$, CN, $NHCOR_5$, $OCOR_4$, furyl or a phenyl group optionally substituted with one or two halogens, $C_1$-$C_2$ alkyl or nitro, $C_{1}$-$C_4$ alkenyl optionally substituted with halogen or $C_{1}$-$C_4$ alkoxy, or $C_{1}$-$C_4$ alkynyl; and Z is hydrogen or $C_1$-$C_4$ alkyl. The disclosure further describes the unique method of using the compounds as herbicidal agents and the methods for their preparation.

14 Claims, No Drawings

OXIME DERIVATIVES OF FORMYLPYRIDYL IMIDAZOLINONES, THE HERBICIDAL USE AND METHODS FOR THE PREPARATION THEREOF

BACKGROUND OF THE INVENTION

1. Field of the Invention

The present invention relates to novel oxime derivatives of 5-formylpyridyl imidazolinone compounds, the method of using said compounds as herbicidal agents and the methods for preparing said compounds.

2. Description of the Related Art

By way of background, U.S. Pat. No. 4,798,619 discloses 2-(2-imidazolin-2-yl) pyridine and quinoline compounds of the general formula:

[chemical structure]

wherein Y and Z each represent members selected from the group consisting of hydrogen, halogen, $C_1$-$C_6$ alkyl, $C_1$-$C_4$ hydroxyloweralkyl, $C_1$-$C_6$ alkoxy, $C_1$-$C_4$ alkylthio, phenoxy, $C_1$-$C_4$ haloalkyl, nitro, cyano, $C_1$-$C_4$ alkylamino, diloweralkylamino, $C_1$-$C_4$ alkylsulfonyl group or phenyl optionally substituted with one $C_1$-$C_4$ alkyl, $C_1$-$C_4$ alkoxy or halogen; and when taken together, Y and Z may form a ring in which YZ are represented by the structure: —$(CH_2)_n$—, where n is an integer of 3 or 4, provided that X is hydrogen; or

[chemical structure]
$$-\overset{L}{\underset{}{C}}=\overset{M}{\underset{}{C}}-\overset{Q}{\underset{}{C}}=\overset{R_7}{\underset{}{C}}-.$$

Japanese Patent Application No. J62174-069-A discloses pyridine compounds of the general formula:

[chemical structure]

wherein X may be hydrogen, $C_1$-$C_4$ alkyl, $C_1$-$C_4$ alkoxymethyl, $C_1$-$C_4$ alkylthiomethyl, $C_1$-$C_4$ haloalkyl, $C_1$-$C_4$ alkylsulfonylmethyl, benzyl or an optionally substituted phenyl or pyridyl group and Y is oxygen, sulfur, monosubstituted nitrogen (in which the substituent is $C_1$-$C_4$ alkyl, $C_1$-$C_4$ alkoxy, $C_1$-$C_4$ alkoxycarbonylamino or an optionally substituted phenyl or pyridyl group) or disubstituted carbon. The pyridyloxime, 5-acetyl-2-(4-isopropyl-4-methyl-5-oxo-2-imidazolin-2-yl)-6-methylnicotinic acid, pyridine-5-(O-ethyloxime), is given as an example. However, in practical use, the herbicide activity of this compound is not satisfactory against many commonly encountered weed species. Further, the tolerance of this compound in crop species limits its use at high rates.

SUMMARY OF THE INVENTION

It is therefore an important object of the present invention to provide a novel class of formylpyridine oxime compounds possessing significantly improved herbicidal properties.

Another object is to provide new 5-oximio-2-(2-imidazolin-2-yl) pyridines as selective herbicidal agents.

A further object is to provide improved herbicidal methods using the new oxime derivatives of the 5-formylpyridyl imidazolinone compounds.

Further purposes and objects of the present invention will appear as the specification proceeds.

The foregoing objects are accomplished by providing new 5-oxime derivatives of 5-formylpyridyl imidazolinones. The compounds of this invention are highly active as preemergent and postemergent herbicides. The background of the invention and its departure from the art will be further described hereinbelow.

DETAILED DESCRIPTION OF THE INVENTION

In accordance with the present invention, there are provided novel 5-formylpyridine oximes represented by the following generic formula I:

[chemical structure] (I)

wherein
R is hydrogen,
  $C_1$-$C_6$ alkyl optionally substituted with one of the following groups: $C_1$-$C_3$ alkoxy, halogen, phenyl or furyl
  $C_3$-$C_6$ alkenyl optionally substituted with one of the following groups: $C_1$-$C_3$ alkoxy, halogen or phenyl,
  $C_3$-$C_6$ alkynyl,
  $C_3$-$C_6$ alkynyl, optionally substituted with $C_1$-$C_3$ alkyl $C_3$-$C_6$ cycloal or
  a cation of an alkali metal, ammonium or Organic ammonium;
$R_1$ is $C_1$-$C_4$ alkyl;
$R_2$ is $C_1$-$C_4$ alkyl or $C_3$-$C_6$ cycloalkyl, and when $R_1$ and $R_2$ are taken together with the carbon to which they are attached, they may represent $C_3$-$C_6$ cycloalkyl;
B is hydrogen or $COR_3$, provided that when B is $COR_3$, R is other than hydrogen or a cation;
$R_3$ is $C_1$-$C_4$ alkyl or phenyl optionally substituted with one or two halogens, nitro or methoxy;
Y is hydrogen,
  $C_1$-$C_4$ branched or unbranched alkyl optionally substituted with $C_1$-$C_4$ alkoxy, $C_1$-$C_4$ alkylthiol, halogen, $CO_2R_4$, CN, $NHCOR_4$, $OCOR_4$, furyl or a phenyl group optionally substituted with one or two halogens, $C_1$-$C_2$ alkyl or nitro, $C_1$–$C_4$ alkenyl optionally substituted with halogen,
$C_1$–$C_4$ alkynyl,
$COR_4$ or
$CONHR_4$;

Z is hydrogen or $C_1$–$C_4$ alkyl;

$R_4$ is $C_1$–$C_4$ alkyl;

an N-oxide thereof, when R is not alkenyl or alkynyl and Y is not alkenyl;

an optical isomer thereof, when $R_1$ and $R_2$ represent different substituents;

a tautomer thereof; or an acid-addition salt thereof, when R is other than a cation.

A preferred group of 5-oximio-2-(2-imidazolin-2-yl) pyridine compounds that exhibit excellent herbicidal activity have the structural formula I as described above wherein R is hydrogen, $C_1$–$C_6$ alkyl or a cation of an alkali metal, ammonium or organic ammonium; $R_1$ is methyl; $R_2$ is isopropyl; B is hydrogen; Y is $C_1$–$C_4$ alkyl optionally substituted with $C_1$–$C_4$ alkoxy, $C_1$–$C_4$ alkylthio or phenyl; and Z is hydrogen or methyl; or the acid-addition salt thereof, when R is other than a cation.

A particularly preferred group of 5-oximio-2-(2-imidazolin-2-yl) pyridine compounds of formula I is one wherein R is hydrogen or a cation of an alkali metal, ammonium or organic ammonium; $R_1$ is methyl; $R_2$ is isopropyl; B is hydrogen; Y is $C_1$–$C_2$ alkyl optionally substituted with $C_1$–$C_4$ alkoxy, $C_1$–$C_4$ alkylthio or phenyl; and Z is hydrogen or methyl; or the acid-addition salt thereof when R is hydrogen.

Representative compounds of formula I would include, for example:

5-Formyl-2-(4-isopropyl-4-methyl-5-oxo-2-imidazolin-2-yl)nicotinic acid, pyridine-5-(O-methyloxime);

5-Formyl-2-(4-isopropyl-4-methyl-5-oxo-2-imidazolin-2-yl)nicotinic acid, pyridine-5-(O-ethyloxime);

5-Formyl-2-(4-isopropyl-4-methyl-5-oxo-2-imidazolin-2-yl)-6-methylnicotinicacid, pyridine-5-(O-methyloxime);

5-Formyl-2-(4-isopropyl-4-methyl-5-oxo-2-imidazolin-2-yl)-nicotinic acid, pyridine-5-(O-benzyloxime);

Methyl 5-formyl-2-(4-isopropyl-4-methyl-5-oxo-2-imidazolin-2-yl)-nicotinate, pyridine-5-(O-methyloxime);

Methyl 5-formyl-2-(4-isopropyl-4-methyl-5-oxo-2-imidazolin-2-yl)-6-methylnicotinate, pyridine-5-(O-methyloxime);

Methyl 5-formyl-2-(4-isopropyl-4-methyl-5-oxo-2-imidazolin-2-yl)-nicotinate, pyridine-5-[O-(2-methoxyethyl)oxime];

5-Formyl-2-(4-isopropyl-4-methyl-5-oxo-2-imidazolin-2-yl)nicotinic acid, pyridine-5-[O-(2-methoxyethyl)oxime];

5-Formyl-2-(4-isopropyl-4-methyl-5-oxo-2-imidazolin-2-yl)-nicotinic acid, pyridine-5-(O-oxime);

Methyl 5-formyl-2-(4-isopropyl-4-methyl-5-oxo-2-imidazolin-2-yl)-nicotinate, pyridine-5-(O-allyloxime);

5-Formyl-2-(4-isopropyl-4-methyl-5-oxo-2-imidazolin-2-yl)-nicotinic acid, pyridine-5-(O-allyloxime);

Methyl 5-formyl-2-(4-isopropyl-4-methyl-5-oxo-2-imidazolin-2-yl)-nicotinate, pyridine-5-(O-oxime);

Benzyl 5-formyl-2-(4-isopropyl-4-methyl-5-oxo-2-imidazolin-2-yl)-nicotinate, pyridine-5-(O-acetyloxime);

Benzyl 5-formyl-2-(4-isopropyl-4-methyl-5-oxo-2-imidazolin-2-yl)-nicotinate, pyridine-5-[O-(methylcarbamoyl) oxime];

Benzyl 5-formyl-2-(4-isopropyl-4-methyl-5-oxo-2-imidazolin-2-yl)-nicotinate, pyridine-5-[O-(methylcarbonyl)oxime];

5-Formyl-2-(4-isopropyl-4-methyl-5-oxo-2-imidazolin-2-yl)-nicotinic acid, tetrabutylammonium salt, pyridine-5-(O-oxime);

Methyl 5-formyl-2-(4-isopropyl-4-methyl-5-oxo-2-imidazolin-2-yl)-nicotinate, pyridine-5-(O-isopropyloxime);

Methyl 5-formyl-2-(4-isopropyl-4-methyl-5-oxo-2-imidazolin-2-yl)-nicotinate, pyridine-5-(O-ethyloxime);

5-Formyl-2-(4-isopropyl-4-methyl-5-oxo-2-imidazolin-2-yl)-nicotinic acid, pyridine-5-(O-isopropyloxime);

Methyl 5-formyl-2-(4-isopropyl-4-methyl-5-oxo-2-imidazolin-2-yl)-nicotinate, pyridine-5-(O-benzyloxime);

5-Formyl-2-(4-isopropyl-4-methyl-5-oxo-2-imidazolin-2-yl)-nicotinic acid, pyridine-5-[O-(o-chlorobenzyl)oxime];

5-Formyl-2-(4-isopropyl-4-methyl-5-oxo-2-imidazolin-2-yl)-nicotinic acid, pyridine-5-[O-(o-methylbenzyl)oxime];

5-Formyl-2-(4-isopropyl-4-methyl-5-oxo-2-imidazolin-2-yl)-nicotinic acid, pyridine-5-[O-(m-chlorobenzyl)oxime];

5-Formyl-2-(4-isopropyl-4-methyl-5-oxo-2-imidazolin-2-yl)-nicotinicacid, pyridine-5-{O-[2-(methylthio)ethyl]oxime};

5-Formyl-2-(4-isopropyl-4-methyl-5-oxo-2-imidazolin-2-yl)-nicotinic acid, pyridine-5-(O-2,2,2-trifluoroethyloxime);

5-Formyl-2-(4-isopropyl-4-methyl-5-oxo-2-imidazolin-2-yl)-nicotinic acid, pyridine-5-{O-[2-(ethoxycarbonyl)ethyl]oxime};

5-Formyl-2-(4-isopropyl-4-methyl-5-oxo-2-imidazolin-2-yl)-nicotinic acid, pyridine-5-(O-furfuryloxime);

5-Formyl-2-(4-isopropyl-4-methyl-5-oxo-2-imidazolin-2-yl)-nicotinic acid, pyridine-5-[O-(methylthio) methyloxime];

5-Formyl-2-(4-isopropyl-4-methyl-5-oxo-2-imidazolin-2-yl)-nicotinic acid, pyridine-5-(O-cyanomethyloxime);

5-Formyl-2-(4-isopropyl-4-methyl-5-oxo-2-imidazolin-2-yl)-nicotinic acid, pyridine-5-[O-(2-chloroethyl) oxime];

5-Formyl-2-(4-isopropyl-4-methyl-5-oxo-2-imidazolin-2-yl)-nicotinic acid, pyridine-5-[O-(2-propynyl)oxime];

5-Formyl-2-(4-isopropyl-4-methyl-5-oxo-2-imidazolin-2-yl)-nicotinic acid, pyridine-5-[O-(3-butenyl)oxime];

5-Formyl-2-(4-isopropyl-4-methyl-5-oxo-2-imidazolin-2-yl)-nicotinic acid, pyridine-5-[O-(2-acetoxyethyl) oxime];

5-Formyl-2-(4-isopropyl-4-methyl-5-oxo-2-imidazolin-2-yl)-nicotinic acid, pyridine-5-[O-(2-acetamidoethyl)oxime];

5-Formyl-2-(4-isopropyl-4-methyl-5-oxo-2-imidazolin-2-yl)-nicotinic acid, pyridine-5-[O-(4,4,4-trifluoro-3-butenyl)oxime];

Benzyl 5-formyl-2-(4-isopropyl-4-methyl-5-oxo-2-imidazolin-2-yl)-nicotinate, pyridine-5-(O-methyloxime);

Methyl2-(1-acetyl-4-isopropyl-4-methyl-5-oxo-2-imidazolin-2-yl)-nicotinate, pyridine 5-(O-methyloxime);

Furfuryl 5-formyl-2-(4-isopropyl-4-methyl-5-oxo-2-imidazolin-2-yl)-nicotinate, pyridine-5-(O-methyloxime);

Ethoxyethyl 5-formyl-2-(4-isopropyl-4-methyl-5-oxo-2-imidazolin-2-yl)-nicotinate, pyridine-5-(O-methyloxime);

Allyl 5-formyl-2-(4-isopropyl-4-methyl-5-oxo-2-imidazolin-2-yl)-nicotinate, pyridine-5-(O-methyloxime);

Propargyl 5-formyl-2-(4-isopropyl-4-methyl-5-oxo-2-O-imidazolin-2-yl)-nicotinate, pyridine-5-(O-methyloxime);

Ammonium 5-formyl-2-(4-isopropyl-4-methyl-5-oxo-2-imidazolin-2-yl)-nicotinic acid, pyridine-5-(O-methyloxime);

Sodium 5-formyl-2-(4-isopropyl-4-methyl-5-oxo-2-imidazolin-2-yl)-nicotinic acid, pyridine-5-(O-methyloxime);

5-Formyl-2-(4-isopropyl-4-methyl-5-oxo-2-imidazolin-2-yl)nicotinic acid, pyridine-5-(O-methyloxime), hydrochloride;

2-(4-Ethyl-4-methyl-5-oxo-2-imidazolin-2-yl)-5-formyl-nicotinic acid, pyridine-5-(O-methyloxime); and 6-Ethyl-5-formyl-2-(4-isopropyl-4-methyl-5-oxo-2-imidazolin-2-yl)-nicotinic acid, pyridine-5-(O-methyloxime).

The compounds of formula I may be readily prepared in accordance with the following reaction schemes set forth in Flow Diagrams I and II. As shown below in Flow Diagram I, compounds of Formula I can be prepared by treating a 5-formyl-2-imidazolin-2-yl-nicotinic acid II with an alkoxyamine III, typically as its hydrochloride salt, in an organic amine (such as pyridine) as solvent, wherein Y, Z, R, $R_1$ and $R_2$ are as previously defined.

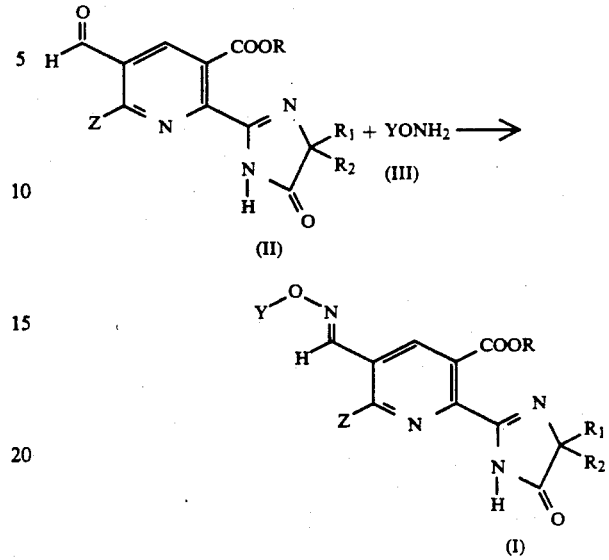

Flow Diagram I

Other methods for preparing the oxime functional group have been widely described in the literature (Sandler and Karo, "Organic Functional Group Preparations III," Chapter (Academic Press, New York 1973)). Many of the alkoxyamines III needed in Flow Diagram I are commercial products and others are prepared by known methods (U.S. Pat. Nos. 4,584,318 and 4,237,123; Takasugi, et. al., *J. Antibiotics.* 36:846 (1983); Grochowski and Jurczak, *Synthesis* 682 (1976); McKay et. al., Canadian J. Chem. 38:343 (1960) and Sandler and Karo, "Organic Functional Group Preparations III," Chapter 10 (Academic Press, New York 1973)).

Compounds of formula I may also be prepared as illustrated below in Flow Diagram II. A 5-formyl-2-imidazolin-2-yl-nicotinic acid II is treated with hydroxylamine, typically as its hydrochloric acid salt, in an organic base, such as pyridine, as solvent to afford 5-oximio derivatives IV. Oximes of formula IV can then be treated with an organic or inorganic base and an electrophilic reagent V, wherein X is halogen or $O_2CR_4$ and $R_4$ is $C_1$-$C_4$ alkyl, to provide oximes of formula I.

Flow Diagram II

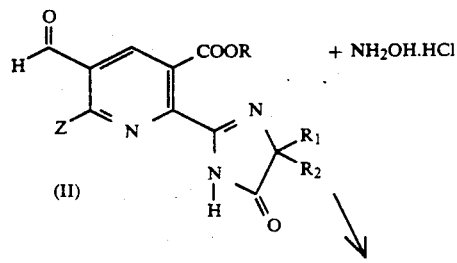

Flow Diagram II

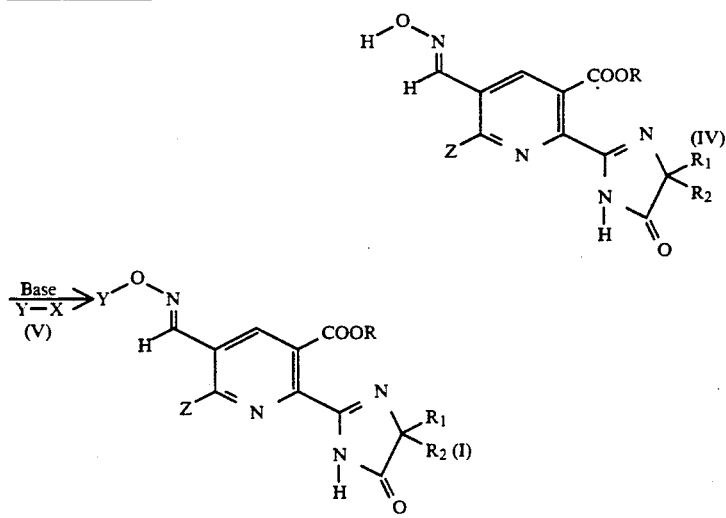

The 5-formyl-2-imidazolin-2-yl-nicotinic acids of formula II may be obtained by the methods outlined below in Flow Diagram III. The 5-formylpyridine acetals VI (where $R_6$ is $C_1$–$C_4$ alkyl) used in Flow Diagram III have been described in U.S. Pat. No. 5,026,859. Compounds of formula VI may be converted to their corresponding 2-imidazolin-2-yl-nicotinic acids VIII by treatment with an aminoamide type VII and a strong base such as potassium tert-butoxide. Compounds of formula VIII can be converted to compounds of formula II where R is hydrogen by treatment with aqueous acid such as 2N hydrochloric acid. Alternatively, formula VIII compounds may be treated sequentially with acetic anhydride, an alkoxide of formula IX, where $R_7$ is $C_1$–$C_4$ alkyl, optionally substituted with aryl or trimethylsilyl, and M is a cationic salt such as, for example, sodium or potassium, to provide nicotinic esters of formula X. Formula X compounds can be converted to 5-formyl-2-imidazolin-2-yl-nicotinic esters of formula II, where R is equal to $R_7$, by treatment with aqueous acid such as 2N hydrochloric acid in a water miscible organic solvent such as tetrahydrofuran or methanol. The compounds of formulas II, VIII and X illustrated in Flow Diagram III have been described in U.S. Pat. No. 5,039,333.

FLOW DIAGRAM III

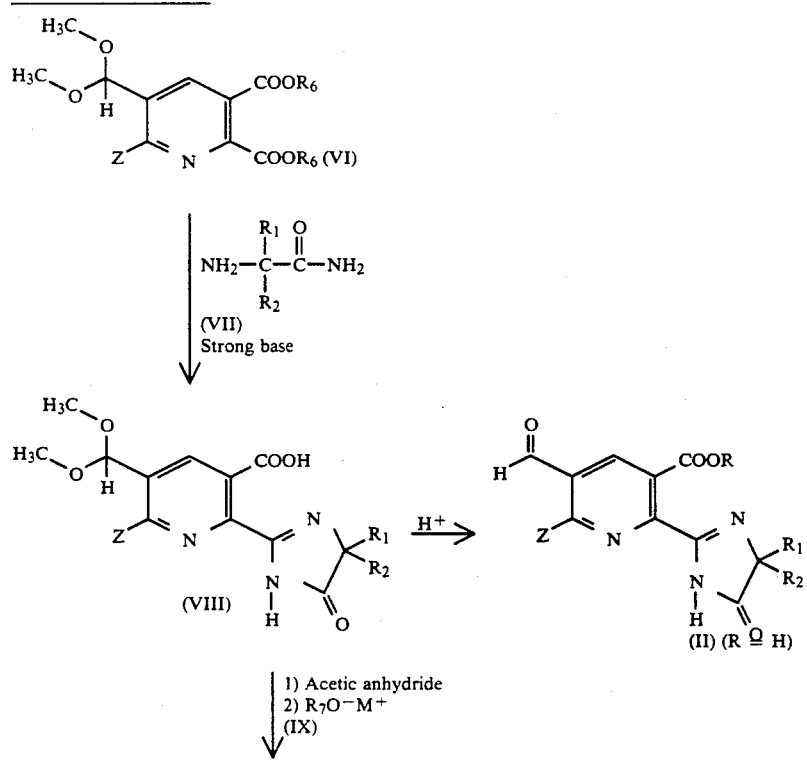

FLOW DIAGRAM III

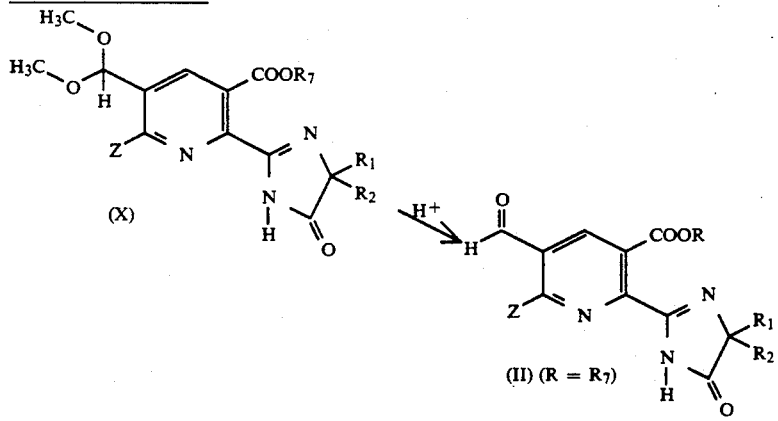

Oximes of formula XI may be converted to their corresponding 5-oximino nicotinic acid of formula I by using standard deesterification methods (Greene, "Protective Groups in Organic Synthesis" (John Wiley & Sons, New York 1978)) as shown below in Flow Diagram IV.

FLOW DIAGRAM IV

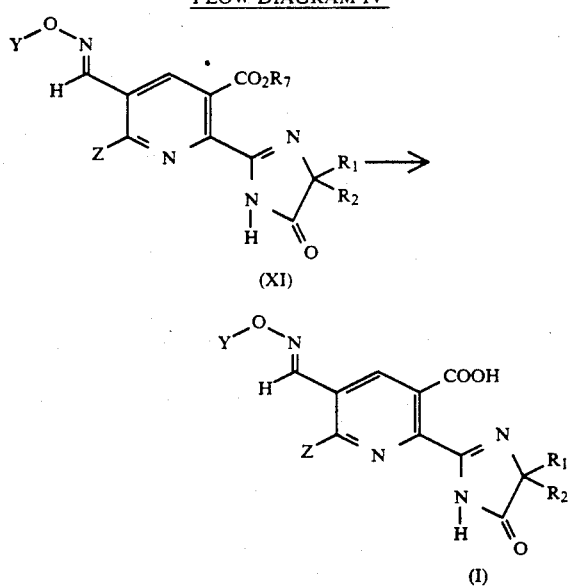

It is generally preferred that the respective product of each process step, described hereinabove, is separated and/or isolated prior to its use as starting material for subsequent steps. Separation and isolation can be effected by any suitable purification procedure such as, for example, evaporation, crystallization, column chromatography, thinlayer chromatography, distillation, etc. It should be appreciated that when typical reaction conditions (e.g., temperatures, mole ratios, reaction times) have been given, the conditions that are either above or below the specified ranges can also be used, though generally less conveniently. While preferred reactants have been identified herein, it is further contemplated that the present invention would include chemical equivalents to each reactant specifically enumerated in this disclosure.

The salt forming moieties of the present invention which are agronomically acceptable include cation-containing compounds such as the alkali metals (e.g. sodium, potassium, etc.); ammonium or organic ammonium. The organic bases of the present invention additionally form agronomically acceptable acid-addition salts with a variety of organic and inorganic salt forming reagents. Such acid addition salts are formed by admixture of the organic free base with one or two equivalents of an acid, preferably in a neutral solvent. Suitable acids include, but are not limited to, sulfuric, phosphoric, hydrochloric, hydroiodic, sulfamic, citric, lactic, fumaric, succinic, tartaric, acetic, benzoic, gluconic, ascorbic and the like. For purposes of this invention, the free bases are equivalent to their cation and acid-addition salts.

The present invention further includes agriculturally suitable compositions containing the compounds of formula I and the use thereof as preemergent or postemergent herbicides. Surprisingly, compounds of this invention display excellent herbicidal activity controlling more weed species at much lower rates than those previously described in the art.

The formula I compounds of this invention are exceedingly effective herbicidal agents which are useful for the control of an exceptionally wide variety of herbaceous and woody annula as well as perennial monocotyledonous and dicotyledonous plants. Moreover, these compounds are herbicidally effective for controlling weeds indigenous to both dry land and wet land areas and are also useful as aquatic herbicides. They are unique in their effectiveness in controlling the abovesaid plants when applied to the foliage thereof or to the soil or water containing seeds or other propagating organs of said plants such as tubers, rhizomes or stolons and when employed at a wide range of application, but generally at rates of from about 0.012 kg per hectare to about 1.00 kg per hectare, and preferably at rates from about 0.012 kg per hectare to about 0.250 kg per hectare.

It is, of course, obvious that rates of application that are either above or below the specified range can also be used to kill undesirable plant species, though generally less favorably. While effective, rates of application of toxicant above the level necessary to kill the undesirable plants should be avoided since application of excessive amounts of toxicant is costly and serves no useful function in the environment.

Among the plants which may be controlled with the compounds of this invention are, for example: *Elatine*

*triandra, Sagittaria pygmaea, Scirpus hotarui, Cyperus serotinus, Eclipta alba, Cyperus difformis, Rotala indica, Lindernia pyridoria, Echinochloa crus-galli, Digitaria sanguinalis, Setaria viridis, Cyperus rotundus, Convolvulus arvensis, Agropyron repens, Datura stramonium, Alopecurus myosuroides, Ipomea spp. Sida sponosa, Ambrosia artemisiifolia, Eichhornia crassipes, Xanthium pensylvanicum, Sesbania exaltata, Avena fatua, Abutilon theophrasti, Bromus tectorum, Sorghum halepense, Lolium spp., Panicum dichotomiflorum, Matricaria spp., Amaranthus retroflexus, Cirsium arvense* and *Rumes japonicus.*

In practice, it has been found that generally the formula (I) pyridines are best suited for use as broad spectrum herbicides, whether employed preemergence or postemergence to the locus in which weed control is desired. This is not to say, however, that all of the formula (I) pyridines are non-selective. Actually, some of the pyridines are selective in leguminous crops, such as soybeans. Similarly, it has been generally found that the formula I compounds are selective herbicides, particularly effective for controlling undesirable weeds in the presence of other crops such as wheat, rice, corn and the like. However, certain of the formula I compounds are less selective than others.

Since the acid-addition or cation salts of the compounds of formula I are water soluble, these compounds can simply be dispersed in water and applied as a dilute aqueous spray to the foliage of plants or to the soil containing the propagating organs thereof. The formula I pyridines, either as the salt or the base, can be formulated with conventional, agronomically acceptable carriers as wettable powders, flowable concentrates, emulsifiable concentrates, granular formulations or the like.

Wettable powders can be prepared by grinding together about 20% to 45% by weight of a finely divided carrier such as kaolin, bentonite, diatomaceous earth, attapulgite or the like, varying amounts of the active compound but typically about 45% to 80% by weight of the active compound, 2% to 5% by weight of a dispersing agent such as sodium lignosulfonate and 2% to 5% by weight of a nonionic surfactant, such as octylphenoxy polyethoxy ethanol, nonylphenoxy polyethoxy ethanol or the like.

A typical flowable liquid can be prepared by admixing about 40% by weight of the active ingredient with about 2% by weight of a gelling agent such as bentonite, 3% by weight of a dispersing agent such as sodium lignosulfonate, 1% by weight of polyethylene glycol and 54% by weight of water.

A typical emulsifiable concentrate can be prepared by dissolving about 5% to 25% by weight of the active ingredient in about 65% to 90% by weight of N-methylpyrrolidone, isophorone, butyl cellosolve, methylacetate or the like an dispersing therein about 5% to 10% by weight of a nonionic surfactant such as an alkylphenoxy polyethoxy alcohol. This concentrate is dispersed in water for application as a liquid spray.

When the compounds of the invention are to be used as herbicides where soil treatments are involved, the compounds may be prepared and applied as granular products. Preparation of the granular product can be achieved by dissolving the active compound in a solvent such as methylene chloride, N-methylpyrrolidone or the like and spraying the thus prepared solution on a granular carrier such as corncob grits, sand, attapulgite, kaolin or the like. The granular product generally comprises about 3% to 20% by weight of the active ingredient and about 97% to 80% by weight of the granular carrier.

As used herein, the term "percent" or "%" refers to weight percent and the terms "mole" or "moles" refer to gram moles. Conventional terminology has further been employed herein where the term "mp" refers to melting point, the term "IR spectrum" refers to the infra-red spectrum and the term "NMR spectrum" refers to the nuclear magnetic resonance spectrum.

A further understanding of the present invention can be obtained from the following examples. However, the examples are set forth only for the illustration of certain aspects of the invention and are not to be construed as limitations thereon. Unless otherwise expressed, all parts are by weight.

EXAMPLE 1

PREPARATION OF DIETHYL 5-FORMYL-6-METHYL-2,3-PYRIDINEDICARBOXYLATE. 5-DIMETHYL ACETAL

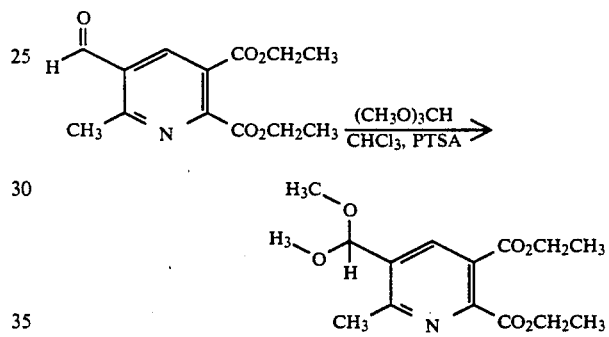

A solution of diethyl 5-formyl-6-methyl-2,3-pyridinedicarboxylate (0.93 g, 0.0035 mol) in chloroform (10 mL) and trimethylorthoformate (1 mL) containing catalytic amounts of methanol (4 drops) and oara-toluenesulfonic acid is stirred for 30 minutes at room temperature and for 1 hour at reflux. The reaction is concentrated in vacuo, redissolved in methylene chloride (25 mL) and washed with saturated sodium bicarbonate (30 mL). The aqueous solution is extracted with additional methylene chloride and the combined organic solutions are dried and concentrated in vacuo. The product is purified by chromatography using silica gel and gradient elution with hexanes/ethyl acetate (6:1 to 4:1) to yield the title compound (0.67 g, 0.0022 mol, 61% yield) as a clear oil, identified by IR and NMR spectral analyses.

EXAMPLE 2

PREPARATION OF 5-FORMYL-2-(4-ISOPROPYL-4-METHYL-5-OXO-2-IMIDAZOLIN-2-YL)-6-METHYLNICOTINIC ACID, 5-(DIMETHYL ACETAL)

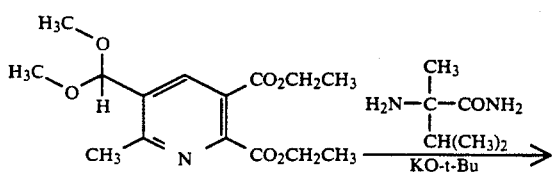

-continued

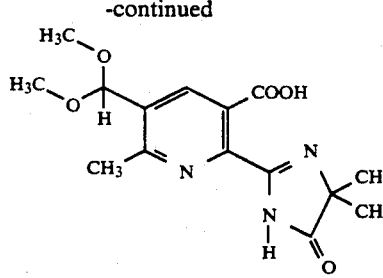

Potassium tert-butoxide (1.39 g, 12.4 mmol) is added to a stirred solution of dimethyl 5-formyl-6-methyl-2,3-pyridinedicarboxylate, 5-(dimethyl acetal) (1.93 g, 6.2 mmol) and 2-amino-2,3-dimethylbutyramide (0.81 g, 6.2 mmol) in toluene (25 mL). The reaction is heated at 80° C. for 1 hour, cooled to room temperature and diluted with water (20 mL). The layers are separated and the aqueous solution acidified to pH 3.0 with 2N hydrochloric acid. The aqueous solution is extracted with methylene chloride (3×30 mL), the extracts dried over anhydrous magnesium sulfate and concentrated in vacuo to give the title compound as an orange solid (1.56 g, 4.5 mmol, 72% yield), mp 147°-150° C., identified by IR and NMR spectral analyses.

EXAMPLE 3

PREPARATION OF 5-FORMYL-2-(4-ISOPROPYL-4-METHYL-5-OXO-2-IMIDAZOLIN-2-YL-)NICOTINIC ACID

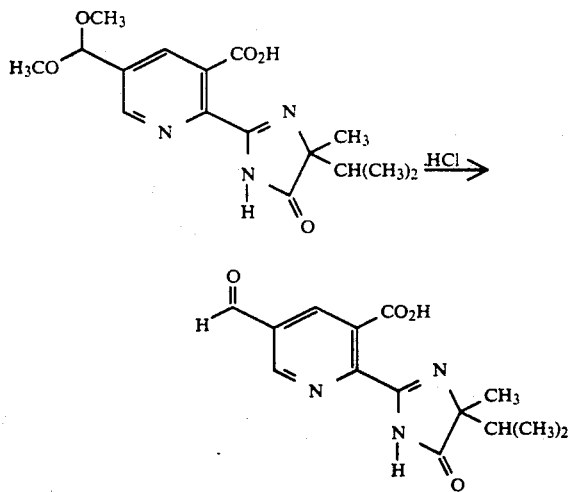

A solution of 5-formyl-2-(4-isopropyl-4-methyl-5-oxo-2-imidazolin-2-yl)nicotinic acid, 5-(dimethyl acetal) (3.65 g, 0.0109 mol) and 2N hydrochloric acid is stirred for 2 hours at room temperature. The pH of the reaction mixture is adjusted to 3.0 with sodium bicarbonate and the water is evaporated in vacuo to give a solid. The solid is triturated with acetone/ethanol (2:1) and removed by filtration. The filtrate is concentrated in vacuo to yield the title compound as a tan solid (3.5 g, 100% yield), mp 187°-198° C., identified by IR and NMR spectral analyses.

EXAMPLE 4

PREPARATION OF METHYL 5-FORMYL-2-(4-ISOPROPYL-4-METHYL-5-OXO-2-IMIDAZOLIN-2-YL)-6-METHYLNICOTINATE, 5-(DIMETHYL ACETAL)

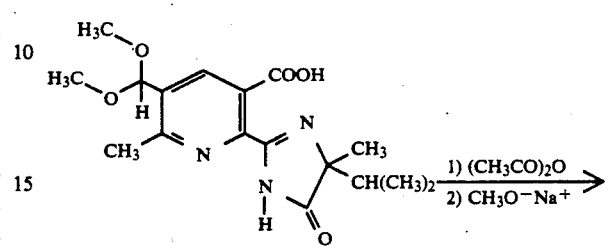

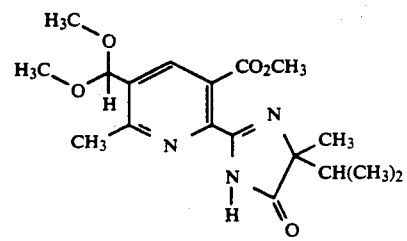

A solution of 5-formyl-2-(4-isopropyl-4-methyl-5-oxo-2-imidazolin-2-yl)-6-methyl-nicotinic acid, 5-(dimethyl acetal) (1.56 g, 4.5 mmol) in acetic anhydride (0.6 mL) and toluene (20 mL) containing 4 drops of pyridine is stirred at 70° C. for 1 hour and at 110° C. for 2 hours. The reaction is concentrated in vacuo, the product is dissolved in methanol (10 mL) and is added to a solution of sodium methoxide (0.48 g, 9.0 mmol) in methanol (30 mL). The resulting solution is stirred at room temperature for 16 hours, quenched with acetic acid (0.65 mL) and concentrated in vacuo. The product is dissolved in methylene chloride (100 mL) and washed with aqueous saturated sodium bicarbonate (100 mL). The aqueous solution was extracted with additional methylene chloride (25 mL) and the combined organics dried over anhydrous magnesium sulfate and concentrated in vacuo to afford the title compound as a yellow solid (1.43 g, 3.9 mmol, 88% yield), mp 42°-51° C., identified by IR and NMR spectral analyses.

EXAMPLE 5

PREPARATION OF METHYL 5-FORMYL-2-(4-ISOPROPYL-4-METHYL-5-OXO-2-IMIDAZOLIN-2-YL)-6-METHYL-NICOTINATE

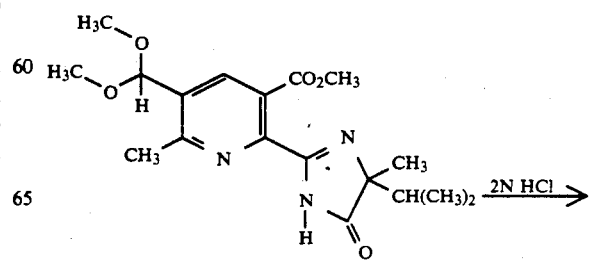

-continued

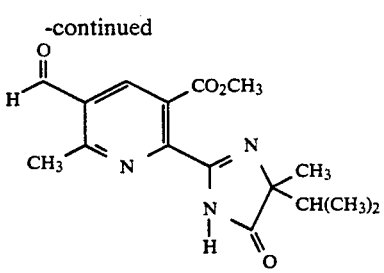

A solution of methyl 5-formyl-2-(4-isopropyl-4-methyl-5-oxo-2-imidazolin-2-yl)-6-methyl-nicotinate, 5-(dimethyl acetal) (1.12 g, 3.1 mmol) in tetrahydrofuran (5 mL) and 2N hydrochloric acid (20 mL) is stirred at room temperature for 2.5 hours. The tetrahydrofuran is removed in vacuo and the aqueous solution basified with aqueous saturated sodium bicarbonate. The aqueous solution is extracted with methylene chloride (2×50 mL). The organic solution is dried over anhydrous magnesium sulfate, concentrated vacuo and purified by chromatography using silica gel and gradient elution with hexanes/ethyl acetate (3:1 to 1:1) to afford the title compound as a white solid (0.76 g, 2.4 mmol, 78% yield), mp 145°-146° C., identified by IR and NMR spectral analyses.

EXAMPLE 6

PREPARATION OF METHYL 5-FORMYL-2-(4-ISOPROPYL-4-METHYL-5-OXO-2-IMIDAZOLIN-2-YL)-6-METHYL-NICOTINATE, PYRIDINE-5-(O-METHYLOXIME)

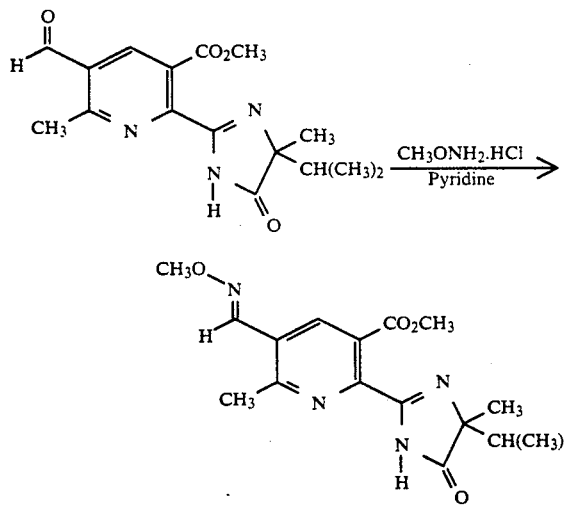

To a solution of methyl 5-formyl-2-(4-isopropyl-4-methyl-5-oxo-2-imidazolin-2-yl)-6-methyl-nicotinate(0.60g, 1.9 mmol) in pyridine (12 mL) is added methoxyamine hydrochloride (0.21 g, 2.5 mmol). The resulting solution is stirred for 40 minutes at room temperature. The pyridine is concentrated in vacuo and the product partitioned between methylene chloride (25 mL) and 2N hydrochloric acid (30 mL). The layers are separated, the aqueous solution extracted with additional methylene chloride and the combined methylene chloride solutions are dried over anhydrous magnesium sulfate and concentrated in vacuo. Chromatography using silica gel and hexanes/ethyl acetate (3:1 to 2:1) as elutant affords the title compound as a white solid (0.55 g, 1.6 mmol, 85% yield), mp 150°-151° C., identified by IR and NMR spectral analyses.

EXAMPLE 7

PREPARATION OF BENZYL 5-FORMYL-2-(4-ISOPROPYL-4-METHYL-5-OXO-2-IMIDAZOLIN-2-YL)-NICOTINATE. PYRIDINE-5-(O-ACETYLOXIME)

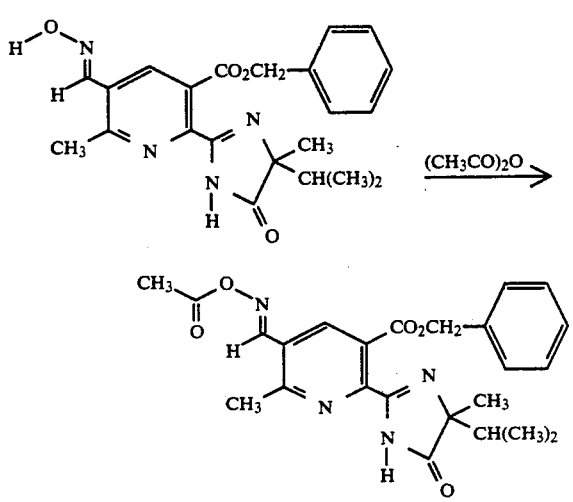

To a solution of benzyl 5-formyl-2-(4-isopropyl-4-methyl-5-oxo-2-imidazolin-2-yl)nicotinate, 5-oxime (0.70 g, 1.8 mmol) in methylene chloride (2.8 mL) plus a catalytic agent triethylamine at 0° C. is added acetic anhydride (0.18 mL, 2 mmol) in methylene chloride (2.8 mL). The reaction is stirred for 2 hours at 0° C., concentrated in vacuo and purified by chromatography using silica gel and 2% methanol in methylene chloride to give the title compound as a white solid (0.67 g, 1.5 mmol, 86% yield), mp 120°-122° C., identified by IR and NMR spectral analyses.

Employing the procedures of Examples 6 and 7, and the corresponding, appropriately substituted starting material, the following compounds in Table I may be obtained.

TABLE I

| Y | Z | R | mp (°C.) |
|---|---|---|---|
| $C_6H_5CH_2$ | H | $CH_3$ | 130-132 |
| $CH_3$ | $CH_3$ | $CH_3$ | 120-140 mixture 3:1 (E:Z) |
| $CH_3$ (E) | $CH_3$ | $CH_3$ | 150-151 |
| 2-$ClC_6H_4CH_2$ | H | $(CH_3)_3SiCH_2CH_2$ | 146-148 |
| 3-$ClC_6H_4CH_2$ | H | $(CH_3)_3SiCH_2CH_2$ | — |
| $CH_2$=$CHCH_2$ | H | $CH_3$ | 117 |
| H | H | $CH_3$ | 192-193.5 |
| $CH_3$ | H | $CH_3$ | 190-191 |
| H | H | $C_6H_5CH_2$ | 185-187 |
| $CH_3CO$ | H | $C_6H_5CH_2$ | 120-122 |
| $CH_3NHCO$ | H | $C_6H_5CH_2$ | gum |
| $CH_3OCO$ | H | $C_6H_5CH_2$ | gum |

TABLE I-continued

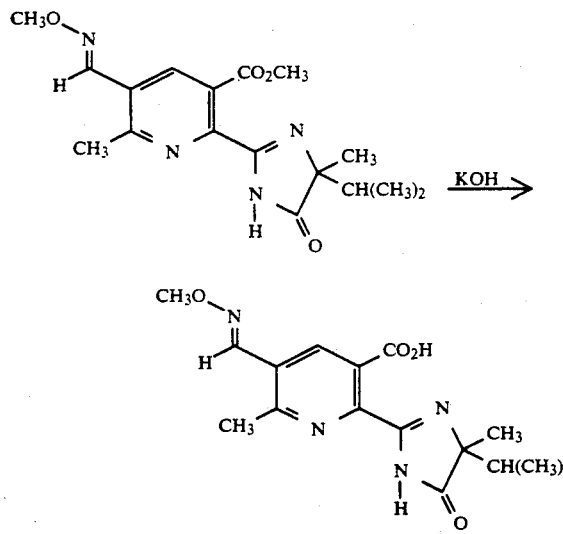

| Y | Z | R | mp (°C.) |
|---|---|---|---|
| H | H | (CH₃)₃SiCH₂CH₂ | 181.5–182.5 |
| CH₃CO | H | (CH₃)₃SiCH₂CH₂ | 114–117 |
| H | H | (CH₃)₄N⁺ | oil |
| (CH₃)₂CH | H | CH₃ | oil |
| CH₃CH₂ | H | CH₃ | 116–118 |
| C₆H₅CH₂ | H | CH₃ | 130–132 |
| 2-CH₃C₆H₄CH₂ | H | (CH₃)₃SiCH₂CH₂ | 152–154 |

EXAMPLE 8

PREPARATION OF 5-FORMYL-2-(4-ISOPROPYL-4-METHYL-5-OXO-2-IMIDAZOLIN-2-YL)-6-METHYL-NICOTINIC ACID, PYRIDINE-5-(O-METHYLOXIME)

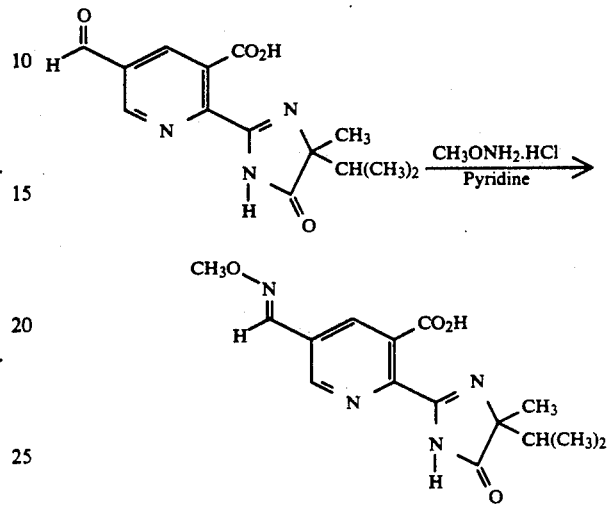

A solution of methyl 5-formyl-2-(4-isopropyl-4-methyl-oxo-2-imidazolin-2-yl)-6-methyl-nicotinate, 5-(O-methyloxime) (0.40 g, 1.16 mmol) in tetrahydrofuran (5 mL) and 0.84N potassium hydroxide (4 mL) is stirred for 30 minutes at 0° C., for 15 minutes at 0° C. to 10° C. and for 3.5 hours at 10° C. The reaction is neutralized with 1.97N hydrochloric acid (1.7 mL) and the tetrahydrofuran removed in vacuo. The aqueous solution is extracted with methylene chloride. The organic solution is dried over anhydrous magnesium sulfate and concentrated in vacuo to afford the title compound as a white solid (0.42 g, 1.2 mmol, 100% yield), mp 177°–180° C., identified by IR and NMR spectral analyses.

EXAMPLE 9

PREPARATION OF 5-FORMYL-2-(4-ISOPROPYL-4-METHYL-5-OXO-2-IMIDAZOLIN-2-YL)-NICOTINIC ACID, PYRIDINE-5-(O-METHYLOXIME)

A solution of 5-formyl-2-(4-isopropyl-4-methyl-5-oxo-2-imidazolin-2-yl)-nicotinic acid (0.39 g, 1.35 mmol) and methoxyamine hydrochloride (0.20 g, 2.39 mmol) in pyridine (5 mL) is stirred for 1.5 hours at room temperature. The pyridine solution is concentrated in vacuo and the reaction mixture is partitioned between methylene chloride (20 mL) and water (20 mL). The layers are separated, the aqueous solution is acidified to pH 3.05 with 2N hydrochloric acid and extracted with additional methylene chloride (2×15 mL). The combined methylene chloride extracts are dried over anhydrous magnesium sulfate and concentrated in vacuo to afford the title compound as a pale yellow solid (0.33 g, 1.04 mmol, 77% yield), mp 221°–226° C., identified by IR and NMR spectral analyses. Employing the procedures of Examples 8 and 9, and the corresponding, appropriately substituted starting material, the following compounds in Table II may be obtained.

TABLE II

| Z | Y | mp (°C.) |
|---|---|---|
| H | CH₃ | 212–213° |
| CH₃ | CH₃ | 177–180° |
| H | CH₂CH₃ | 204–206° |
| H | CH(CH₃)₂ | 122–123° |
| H | CH₂CH=CH₂ | 195–197° |
| H | H | 230–232° |
| H | CH₂CH₂OCH₃ | 203–205° |
| H | CH₂CH₂SCH₃ | 189–194° |
| H | CH₂C₆H₅ | 193–195° |
| H | CH₂—(2-Cl)C₆H₄ | 204–207° |
| H | CH₂—(3-Cl)C₆H₄ | 203–205° |

TABLE II-continued

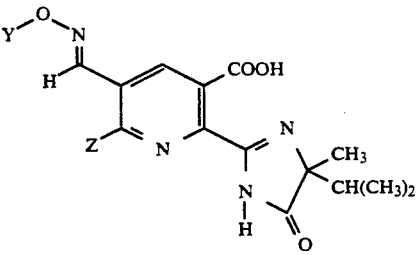

| Z | Y | mp (°C.) |
|---|---|---|
| H | CH$_2$(2-CH$_3$)C$_6$H$_4$ | 211–213° |

EXAMPLE 10

Preemergence Herbicidal Evaluation of Test Compounds

To evaluate the preemergence herbicidal activity of representative compounds of the present invention, the seeds of a variety of monocotyledonous and dicotyledonous plants are separately mixed with potting soil and planted on top of approximately one inch of soil in separate pint cups. After planting, the cups are sprayed with the selected aqueous acetone solution containing the test compound in sufficient quantity to provide the equivalent of about 0.250 kg per hectare and about 0.500 kg per hectare of test compound per cup. The treated cups are then placed on greenhouse benches, watered and cared for in accordance with conventional greenhouse procedures. From four to five weeks after treatment, the tests are terminated and each cup is examined and rated according to the rating system set forth below.

Plant species employed in these evaluations are reported by header abbreviation, common name and scientific name. Compounds employed in the preemergence herbicidal evaluation and in the postemergence evaluation in the following example are given a compound number and identified by name. Data obtained are reported in Table III below by compound number. Where more than one test is involved for a given compound, the data are averaged.

Herbicide Rating Scale

Results of herbicide evaluation are expressed on a rating scale (0–9). The scale is based upon a visual observation of plant stand, vigor, malformation, size, chlorosis and overall plant appearance as compared with a control.

| RATING | MEANING | % Control (COMPARED TO CHECK) |
|---|---|---|
| 9 | Complete Kill | 100 |
| 8 | Approaching Complete Kill | 91–99 |
| 7 | Good Herbicidal Effect | 80–90 |
| 6 | Herbicidal Effect | 65–79 |
| 5 | Definite Injury | 45–64 |
| 4 | Injury | 30–44 |
| 3 | Moderate Effect | 16–29 |
| 2 | Slight Effect | 6–15 |
| 1 | Trace Effect | 1–5 |
| 0 | No Effect | 0 |

| PLANT SPECIES EMPLOYED IN HERBICIDAL EVALUATIONS | | |
|---|---|---|
| HEADER ABB | COMMON NAME | SCIENTIFIC NAME |
| BARNYARDGR | BARNYARDGRASS | ECHINOCHLOA CRUS-GALLI, (L)BEAU |
| FOXTAIL | FOXTAIL SPP. | SETARIA SPP. |
| P NUTSEDGE | NUTSEDGE, PURPLE | CYPERUS RONTUNDUS, L. |
| WILD OATS | OAT, WILD | AVENA FATUA, L. |
| QUACKGRASS | QUACKGRASS | AGROPYRON REPENS, (L)BEAUV. |
| FIELD BINDWD | BINDWEED, FIELD (RHIZOME) | CONVOLVULUS ARVENSIS, L. |
| MORNING GLRY | MORNING GLORY SPP. | IPOMEA SPP. |
| RAGWEED | RAGWEED, COMMON | AMBROSIA ARTEMISIIFOLIA, L. |
| WILD MUSTD | MUSTARD, WILD | BRASSICA KABER, (DC)L.C. WHEELR |
| VELVETLEAF | VELVETLEAF | ABUTILON THEOPHRASTI, MEDIC. |
| SUGARBEETS | SUGARBEETS | BETA VULGARIS, L. |
| CORN FIELD | CORN, FIELD | ZEA MAYS, L. |
| COTTON | COTTON | GOSSYPIUM HIRSUTUM, L. |
| SOYBEAN BR | SOYBEAN, BROWN | GLYCINE SOJA |
| SOYBEAN WI | SOYBEAN, WHITE | GLYCINE SOJA |

| COMPOUNDS EVALUATED AS HERBICIDAL AGENTS | |
|---|---|
| COMPOUND NUMBER | |
| 1 | 5-formyl-2-(4-isopropyl-4-methyl-5-oxo-2-imidazolin-2-yl)-nicotinic acid, pyridine-5-(O-methyloxime) |
| 2 | 5-formyl-2-(4-isopropyl-4-methyl-5-oxo-2-imidazolin-2-yl)-nicotinic acid, pyridine-5-(O-ethyloxime) |
| 3 | (E)-5-formyl-2-(4-isopropyl-4-methyl-5-oxo-2-imidazolin-2-yl)-6-methylnicotinic acid, pyridine-5-(O-methyloxime) |
| 4 | 5-formyl-2-(4-isopropyl-4-methyl-5-oxo-2-imidazolin-2-yl)-nicotinic acid, pyridine-5-(O-benzyloxime) |
| 5 | 5-Formyl-2-(4-isopropyl-4-methyl-5-oxo-2-imidazolin-2-yl)-nicotinic acid, |

-continued

COMPOUNDS EVALUATED AS HERBICIDAL AGENTS

| COMPOUND NUMBER | |
|---|---|
| | pyridine-5-(O-oxime) |
| 6 | Methyl 5-formyl-2-(4-isopropyl-4-methyl-5-oxo-2-imidazolin-2-yl)-nicotinate, pyridine-5-(O-allyloxime) |
| 7 | 5-Formyl-2-(4-isopropyl-4-methyl-5-oxo-2-imidazolin-2-yl)-nicotinic acid, pyridine-5-(O-allyloxime) |
| 8 | Methyl 5-formyl-2-(4-isopropyl-4-methyl-5-oxo-2-imidazolin-2-yl)-nicotinate, pyridine-5-(O-oxime) |
| 9 | Methyl 5-formyl-2-(4-isopropyl-4-methyl-5-oxo-2-imidazolin-2-yl)-nicotinate, pyridine-5-(O-methyloxime) |
| 10 | Methyl 5-formyl-2-(4-isopropyl-4-methyl-5-oxo-2-imidazolin-2-yl)-nicotinate, pyridine-5-(O-isopropyloxime) |
| 11 | Methyl 5-formyl-2-(4-isopropyl-4-methyl-5-oxo-2-imidazolin-2-yl)-nicotinate, pyridine-5-(O-ethyloxime) |
| 12 | 5-Formyl-2-(4-isopropyl-4-methyl-5-oxo-2-imidazolin-2-yl)-nicotinic acid, pyridine-5-(O-isopropyloxime) |
| 13 | Methyl 5-formyl-2-(4-isopropyl-4-methyl-5-oxo-2-imidazolin-2-yl)-nicotinate, pyridine-5-(O-benzyloxime) |
| 14 | Methyl 5-formyl-2-(4-isopropyl-4-methyl-5-oxo-2-imidazolin-2-yl)-6-methylnicotinate, pyridine-5-(O-methyloxime) (3:1 mixture of (E) and (Z) isomers) |
| 15 | 5-Formyl-2-(4-isopropyl-4-methyl-5-oxo-2-imidazolin-2-yl)-nicotinic acid, pyridine-5-[O-(o-chlorobenzyl)oxime] |
| 16 | 5-Formyl-2-(4-isopropyl-4-methyl-5-oxo-2-imidazolin-2-yl)-nicotinic acid, pyridine-5-[O-(o-methylbenzyl)oxime] |
| 17 | 5-Formyl-2-(4-isopropyl-4-methyl-5-oxo-2-imidazolin-2-yl)-nicotinic acid, pyridine-5-[O-(m-chlorobenzyl)oxime] |
| 18 | 5-Formyl-2-(4-isopropyl-4-methyl-5-oxo-2-imidazolin-2-yl)-nicotinic acid, pyridine-5-{O-[2-(methylthio)ethyl]oxime} |
| 19 | 5-Formyl-2-(4-isopropyl-4-methyl-5-oxo-2-imidazolin-2-yl)-nicotinic acid, pyridine-5-[O-(2-methoxyethyl)oxime]; |

TABLE III

PREEMERGENCE TESTS - RATES IN KG/HA

| COMPOUND NO. | RATE | BARN YARDGR | FOX TAIL | P NUT SEDGE | WILD OATS | QUACK GRASS | FIELD BINDWD | MORNING GLRY | RAG WEED |
|---|---|---|---|---|---|---|---|---|---|
| 1 | 0.500 | 9.0 | 9.0 | 9.0 | 8.0 | 9.0 | 9.0 | 9.0 | 9.0 |
|   | 0.250 | 9.0 | 9.0 | 9.0 | 8.0 | 9.0 | 9.0 | 9.0 | 9.0 |
| 2 | 0.500 | 9.0 | 9.0 | 7.0 | 6.0 | 9.0 | 9.0 | 7.0 | 6.0 |
|   | 0.250 | 6.0 | 9.0 | 7.0 | 9.0 | 9.0 | 9.0 | 7.0 | 4.0 |
| 3 | 0.500 | 6.0 | 9.0 | 9.0 | 9.0 | 9.0 | 9.0 | 7.0 | 8.0 |
|   | 0.250 | 6.0 | 9.0 | 9.0 | 9.0 | 9.0 | 9.0 | 8.0 | 7.0 |
| 4 | 0.500 | 4.5* | 8.0 | 4.5* | 5.5* | 8.0 | 8.5 | 4.5* | 4.5* |
|   | 0.250 | 4.5* | 7.5 | 4.5* | 4.5* | 6.0* | 5.5* | 4.5* | 4.0* |
| 5 | 0.500 | 0.0 | 0.0 | 9.0 | 0.0 | 9.0 | 9.0 | 7.0 | 0.0 |
|   | 0.250 | 0.0 | 0.0 | 9.0 | 0.0 | 9.0 | 9.0 | 6.0 | 0.0 |
| 6 | 0.500 | 0.0 | 0.0 | 0.0 | 0.0 | 0.0 | 7.0 | 0.0 | 0.0 |
|   | 0.250 | 0.0 | 0.0 | 0.0 | 0.0 | 0.0 | 0.0 | 0.0 | 0.0 |
| 7 | 0.500 | 0.0 | 4.0 | 8.0 | 7.0 | 9.0 | 9.0 | 4.0 | 4.0 |
|   | 0.250 | 0.0 | 4.0 | 0.0 | 0.0 | 9.0 | 9.0 | 0.0 | 0.0 |
| 8 | 0.500 | 0.0 | 0.0 | 0.0 | 0.0 | 0.0 | 7.0 | 0.0 | 0.0 |
|   | 0.250 | 0.0 | 0.0 | 0.0 | 0.0 | 0.0 | 0.0 | 0.0 | 0.0 |
| 9 | 0.500 | 9.0 | 9.0 | 9.0 | 9.0 | 9.0 | 9.0 | 9.0 | 9.0 |
|   | 0.250 | 9.0 | 9.0 | 9.0 | 9.0 | 9.0 | 9.0 | 8.0 | 9.0 |
| 10 | 0.500 | 0.0 | 0.0 | 0.0 | 4.0 | 9.0 | 9.0 | 0.0 | 6.0 |
|    | 0.250 | 0.0 | 0.0 | 0.0 | 1.0 | 8.0 | 9.0 | 0.0 | 2.0 |
| 11 | 0.500 | 4.0 | 7.0 | 6.0 | 9.0 | 9.0 | 9.0 | 4.0 | 7.0 |
|    | 0.250 | 0.0 | 4.0 | 2.0 | 6.0 | 9.0 | 9.0 | 0.0 | 2.0 |
| 12 | 0.500 | 0.0 | 9.0 | 9.0 | 6.0 | 9.0 | 9.0 | 8.0 | 2.0 |
|    | 0.250 | 0.0 | 8.0 | 6.0 | 3.0 | 9.0 | 9.0 | 0.0 | 0.0 |
| 13 | 0.500 | 0.0 | 0.0 | 0.0 | 0.0 | 0.0 | 0.0 | 0.0 | 0.0 |
| 14 | 0.500 | 6.0 | 8.0 | 6.0 | 9.0 | 9.0 | 9.0 | 8.0 | 4.0 |
|    | 0.250 | 2.0 | 0.0 | 2.0 | 9.0 | 9.0 | 9.0 | 5.0 | 2.0 |
| 15 | 0.500 | 0.0 | 0.0 | 0.0 | 0.0 | 0.0 | 0.0 | 0.0 | 0.0 |
| 16 | 0.500 | 0.0 | 0.0 | 0.0 | 0.0 | 0.0 | 9.0 | 0.0 | 0.0 |
|    | 0.250 | 0.0 | 0.0 | 0.0 | 0.0 | 0.0 | 6.0 | 0.0 | 0.0 |
| 17 | 0.500 | 0.0 | 0.0 | 0.0 | 0.0 | 6.0 | 7.0 | 0.0 | 0.0 |
|    | 0.250 | 0.0 | 0.0 | 0.0 | 0.0 | 1.0 | 2.0 | 0.0 | 0.0 |
| 18 | 0.500 | 0.0 | 0.0 | 0.0 | 0.0 | 0.0 | 0.0 | 0.0 | 0.0 |
| 19 | 0.500 |   | 6.0 | — | 6.0 | 9.0 | 9.0 |   |   |
|    | 0.250 |   | — | — | 4.0 | 9.0 | 9.0 |   |   |

| COMPOUND NO. | WILD MSTRD | VELVET LEAF | SUGAR BEETS | CORN FIELD | COTTON | SOYBEAN BR | SOYBEAN WI |
|---|---|---|---|---|---|---|---|
| 1 | 9.0 | 9.0 | 9.0 | 9.0 | 9.0 | 6.0 | 7.0 |
|   | 9.0 | 9.0 | 9.0 | 9.0 | 9.0 | — | 6.0 |
| 2 | 9.0 | 8.0 | 0.0 | 9.0 | 9.0 | 4.0 | 6.0 |
|   | 9.0 | 7.0 | 9.0 | 9.0 | 9.0 | 4.0 | 3.0 |
| 3 | 9.0 | 7.0 | 9.0 | 9.0 | 9.0 | 7.0 | 7.0 |
|   | 9.0 | 7.0 | 9.0 | 9.0 | 7.0 | 2.0 | 3.0 |
| 4 | 8.5 | 4.5* | 7.5 | 4.5* | 4.5* | 4.5* | 4.5* |
|   | 8.5 | 4.5* | 7.5 | 4.5* | 4.5* | 4.0* | 4.0* |
| 5 | 9.0 | 7.0 | 9.0 | 4.0 | 4.0 | 2.0 | 0.0 |

TABLE III-continued

| | PREEMERGENCE TESTS - RATES IN KG/HA | | | | | | |
|---|---|---|---|---|---|---|---|
| | 9.0 | 7.0 | 9.0 | 2.0 | 4.0 | 0.0 | 0.0 |
| 6 | 0.0 | 0.0 | 0.0 | 0.0 | 0.0 | 0.0 | 0.0 |
| | 0.0 | 0.0 | 0.0 | 0.0 | 0.0 | 0.0 | 0.0 |
| 7 | 7.0 | 6.0 | 2.0 | 9.0 | 6.0 | 2.0 | 0.0 |
| | 0.0 | 4.0 | 0.0 | 3.0 | 3.0 | 0.0 | 0.0 |
| 8 | — | 0.0 | 6.0 | 0.0 | 0.0 | 0.0 | 0.0 |
| | 0.0 | 0.0 | 0.0 | 0.0 | 0.0 | 0.0 | 0.0 |
| 9 | 9.0 | 9.0 | 9.0 | 9.0 | 9.0 | 3.0 | 3.0 |
| | 9.0 | 8.0 | 9.0 | 9.0 | 9.0 | 1.0 | 2.0 |
| 10 | 8.0 | 2.0 | 9.0 | 4.0 | 0.0 | 0.0 | 0.0 |
| | 2.0 | 0.0 | 2.0 | 0.0 | 0.0 | 0.0 | 0.0 |
| 11 | 9.0 | 7.0 | 9.0 | 9.0 | 9.0 | 2.0 | 2.0 |
| | 8.0 | 2.0 | 8.0 | 9.0 | 2.0 | 0.0 | 0.0 |
| 12 | 7.0 | 7.0 | 9.0 | 9.0 | 4.0 | 0.0 | 2.0 |
| | 3.0 | 4.0 | 4.0 | 0.0 | 4.0 | 0.0 | 0.0 |
| 13 | 0.0 | 0.0 | 0.0 | 0.0 | 0.0 | 0.0 | 0.0 |
| 14 | 9.0 | 7.0 | 9.0 | 9.0 | 8.0 | 1.0 | 2.0 |
| | 9.0 | 4.0 | 9.0 | 9.0 | 3.0 | 1.0 | 2.0 |
| 15 | 0.0 | 0.0 | 0.0 | 0.0 | 0.0 | 0.0 | 0.0 |
| 16 | 0.0 | 0.0 | 0.0 | 0.0 | 0.0 | 0.0 | 0.0 |
| | 0.0 | 0.0 | 0.0 | 0.0 | 0.0 | 0.0 | 0.0 |
| 17 | 0.0 | 0.0 | 0.0 | 0.0 | 0.0 | 0.0 | 0.0 |
| | 0.0 | 0.0 | 0.0 | 0.0 | 0.0 | 0.0 | 0.0 |
| 18 | 0.0 | 0.0 | 0.0 | 0.0 | 0.0 | 0.0 | 0.0 |
| 19 | — | — | — | 9.0 | | | |
| | 2.0 | 2.0 | 4.0 | 9.0 | | | |

*THE RATINGS AVERAGED HAD A DISCREPANCY OF 6 OR GREATER, BETWEEN TWO OR MORE REPLICATES

EXAMPLE 11

Postemergence Herbicidal Evaluation of Test Compounds

The postemergence herbicidal activity of the compounds of the present invention is determined by the following tests, wherein a variety of monocotyledonous and dicotyledonous plants are treated with test compounds dispersed in aqueous acetone mixtures. In the tests, seedling plants are grown in jiffy flats for about two weeks. The test compounds are dispersed in 50/50 acetone/water mixtures containing 0.5% TWEEN® 20, a polyoxyethylene sorbitan monolaurate surfactant of Atlas Chemical Industries, in sufficient quantities to provide the equivalent of about 0.012 kg per hectare to about 1.0 kg per hectare of active compound when applied to the plants through a spray nozzle operating at 40 psig for a predetermined time. After spraying, the plants are placed on greenhouse benches and are cared for in the usual manner, commensurate with conventional greenhouse practices. From four to five weeks after treatment, the seedling plants are examined and rated according to the rating system provided in Example 10 above. The data obtained are recorded in Table IV below. The compounds evaluated are reported by compound number given in Example 10.

TABLE IV

| | PREEMERGENCE TESTS - RATES IN KG/HA | | | | | | | |
|---|---|---|---|---|---|---|---|---|
| COMPOUND NO. | RATE | BARN YARDGR | FOX TAIL | P NUT SEDGE | WILD OATS | QUACK GRASS | FIELD BINDWD | MORNING GLRY | RAG WEED |
| 1 | 0.095 | 9.0 | 7.0 | 9.0 | 9.0 | 9.0 | 9.0 | 9.0 | 8.0 |
| | 0.048 | 9.0 | 7.0 | 9.0 | 9.0 | 9.0 | 9.0 | 9.0 | 8.0 |
| | 0.024 | 9.0 | 4.0 | 7.0 | 9.0 | 8.0 | 9.0 | 7.0 | 2.0 |
| | 0.012 | 9.0 | 4.0 | 6.0 | 9.0 | 9.0 | 9.0 | 4.0 | 2.0 |
| 2 | 0.125 | 6.0 | 8.0 | 1.0 | 9.0 | 9.0 | 9.0 | 7.0 | 4.0 |
| | 0.063 | 6.0 | 7.0 | 0.0 | 9.0 | 7.0 | 9.0 | 7.0 | 2.0 |
| | 0.032 | 4.0 | 6.0 | 0.0 | 8.0 | 7.0 | 6.0 | 7.0 | 0.0 |
| 3 | 0.250 | 6.0 | 9.0 | 6.0 | 9.0 | 9.0 | 9.0 | 9.0 | 7.0 |
| | 0.125 | 6.0 | 9.0 | 4.0 | 9.0 | 9.0 | 9.0 | 8.0 | 7.0 |
| | 0.063 | 6.0 | 6.0 | 2.0 | 9.0 | 9.0 | 7.0 | 8.0 | 2.0 |
| 4 | 0.500 | 0.0 | 3.0* | 0.0 | 3.0* | 2.0 | 6.0 | 4.0* | 1.0 |
| | 0.250 | 0.0 | 1.0 | 0.0 | 3.0* | 1.0 | 4.0 | 3.5* | 1.0 |
| 5 | 0.125 | 0.0 | 8.0 | 4.0 | 4.0 | 6.0 | 7.0 | 5.0 | 0.0 |
| | 0.063 | 0.0 | 7.0 | 2.0 | 2.0 | 4.0 | 7.0 | 3.0 | 0.0 |
| | 0.032 | 0.0 | 7.0 | 2.0 | 0.0 | 2.0 | 6.0 | 2.0 | 0.0 |
| 6 | 0.500 | 0.0 | 0.0 | 0.0 | 0.0 | 0.0 | 0.0 | 0.0 | 0.0 |
| 7 | 0.125 | 0.0 | 9.0 | 0.0 | 8.0 | 2.0 | 9.0 | 0.0 | 2.0 |
| | 0.063 | 4.0 | 7.0 | 0.0 | 3.0 | 0.0 | 4.0 | 2.0 | 0.0 |
| | 0.032 | 0.0 | 0.0 | 0.0 | 0.0 | 0.0 | 2.0 | 0.0 | 0.0 |
| 8 | 0.500 | 0.0 | 0.0 | 0.0 | 0.0 | 0.0 | 0.0 | 0.0 | 0.0 |
| 9 | 0.250 | 8.0 | 8.0 | 1.0 | 9.0 | 9.0 | 9.0 | 8.0 | 7.0 |
| | 0.125 | 2.0 | 7.0 | 1.0 | 6.0 | 9.0 | 9.0 | 2.0 | 6.0 |
| | 0.063 | 0.0 | 2.0 | 0.0 | 2.0 | 4.0 | 2.0 | 1.0 | 1.0 |
| 10 | 0.500 | 0.0 | 3.0 | 0.0 | 4.0 | 8.0 | 4.0 | 4.0 | 6.0 |
| | 0.250 | 0.0 | 1.0 | 0.0 | 2.0 | 2.0 | 2.0 | 4.0 | 0.0 |
| 12 | 0.125 | — | 8.0 | 4.0 | 8.0 | 8.0 | 9.0 | 2.0 | 3.0 |
| | 0.063 | 2.0 | 7.0 | 2.0 | 8.0 | 8.0 | 9.0 | 2.0 | 2.0 |
| | 0.032 | 2.0 | 2.0 | 2.0 | 7.0 | 5.0 | 9.0 | 2.0 | 2.0 |

TABLE IV-continued

PREEMERGENCE TESTS - RATES IN KG/HA

| | | | | | | | | | |
|---|---|---|---|---|---|---|---|---|---|
| 13 | 1.000 | 0.0 | 0.0 | 0.0 | 0.0 | 0.0 | 0.0 | 0.0 | 0.0 |
|  | 0.500 | 0.0 | 0.0 | 0.0 | 0.0 | 0.0 | 0.0 | 0.0 | 0.0 |
| 14 | 1.000 | 0.0 | 0.0 | 2.0 | 7.0 | 8.0 | 9.0 | 8.0 | 7.0 |
|  | 0.500 | 0.0 | 0.0 | 0.0 | 7.0 | 8.0 | 9.0 | 4.0 | 4.0 |
| 16 | 0.500 | 0.0 | 0.0 | 0.0 | 0.0 | 0.0 | 0.0 | 0.0 | 0.0 |
| 17 | 0.500 | 0.0 | 0.0 | 0.0 | 0.0 | 0.0 | 0.0 | 0.0 | 0.0 |
| 18 | 1.000 | 3.0 | 4.0 | 2.0 | 6.0 | 6.0 | 7.0 | 4.0 | 2.0 |
|  | 0.500 | 0.0 | 2.0 | 0.0 | 6.0 | 4.0 | 4.0 | 4.0 | 0.0 |
| 19 | 0.500 | 5.0 | 9.0 | 2.0 | 9.0 | 9.0 | 9.0 | 8.0 | 6.0 |
|  | 0.250 | — | 9.0 | 2.0 | 9.0 | 9.0 | 9.0 | 8.0 | 2.0 |
|  | 0.125 |  | 8.0 | — | 8.0 | 9.0 | 9.0 | 7.0 |  |
|  | 0.063 |  | 7.0 | — | 8.0 | 9.0 | 4.0 | 4.0 |  |

| COMPOUND NO. | WILD MSTRD | VELVET LEAF | SUGAR BEETS | CORN FIELD | COTTON | SOYBEAN BR | SOYBEAN WI |
|---|---|---|---|---|---|---|---|
| 1 | 9.0 | 8.0 | 9.0 | 9.0 | 9.0 | 4.0 | 6.0 |
|  | 9.0 | 8.0 | 9.0 | 9.0 | 7.0 | 2.0 | 5.0 |
|  | 9.0 | 6.0 | 9.0 | 9.0 | 7.0 | 2.0 | 1.0 |
|  | 9.0 | 6.0 | 9.0 | 9.0 | 7.0 | 1.0 | 0.0 |
| 2 | 9.0 | 9.0 | 9.0 | 9.0 | 8.0 | 7.0 | 8.0 |
|  | 7.0 | 6.0 | 9.0 | 9.0 | 7.0 | 6.0 | 2.0 |
|  | 6.0 | 4.0 | 9.0 | 9.0 | 9.0 | 4.0 | 2.0 |
| 3 | 9.0 | 8.0 | 9.0 | 9.0 | 9.0 | 5.0 | 5.0 |
|  | 9.0 | 7.0 | 9.0 | 9.0 | 8.0 | 2.0 | 3.0 |
|  | 9.0 | 4.0 | 9.0 | 9.0 | 8.0 | 2.0 | 2.0 |
| 4 | 8.0 | 6.5 | 7.5 | 3.5* | 3.0 | 1.0 | 1.0 |
|  | 8.0 | 6.0 | 8.5 | 3.5* | 1.5 | 0.5 | 0.5 |
| 5 | 8.0 | 7.0 | 9.0 | 2.0 | 4.0 | 2.0 | 1.0 |
|  | 8.0 | 7.0 | 9.0 | 2.0 | 2.0 | 1.0 | 0.0 |
|  | 8.0 | 6.0 | 8.0 | 0.0 | 0.0 | 0.0 | 0.0 |
| 6 | 0.0 | 0.0 | 0.0 | 0.0 | 0.0 | 0.0 | 0.0 |
| 7 | 6.0 | 2.0 | 7.0 | 8.0 | 3.0 | 4.0 | 4.0 |
|  | 3.0 | 0.0 | 9.0 | 9.0 | 0.0 | 0.0 | 0.0 |
|  | 3.0 | 2.0 | 8.0 | 7.0 | 9.0 | 0.0 | 0.0 |
| 8 | 0.0 | 0.0 | 0.0 | 0.0 | 0.0 | 0.0 | 0.0 |
| 9 | 9.0 | 7.0 | 9.0 | 9.0 | 8.0 | 2.0 | 3.0 |
|  | 9.0 | — | 9.0 | 9.0 | 8.0 | 1.0 | 2.0 |
|  | 9.0 | 4.0 | 9.0 | 2.0 | 7.0 | 1.0 | 2.0 |
| 10 | 9.0 | 2.0 | 9.0 | 7.0 | 0.0 | 2.0 | 0.0 |
|  | 9.0 | 0.0 | 9.0 | 4.0 | 0.0 | 0.0 | 0.0 |
| 12 | 9.0 | 7.0 | 9.0 | 9.0 | 4.0 | 3.0 | 4.0 |
|  | 8.0 | 6.0 | 9.0 | 9.0 | 2.0 | 2.0 | 2.0 |
|  | 7.0 | 2.0 | 9.0 | 8.0 | 1.0 | 2.0 | 1.0 |
| 13 | 2.0 | 0.0 | 7.0 | 0.0 | 0.0 | 0.0 | 0.0 |
|  | 0.0 | 0.0 | 2.0 | 0.0 | 0.0 | 0.0 | 0.0 |
| 14 | 9.0 | 2.0 | 9.0 | 9.0 | 8.0 | 2.0 | 3.0 |
|  | 9.0 | 2.0 | 9.0 | 9.0 | 7.0 | 2.0 | 2.0 |
| 16 | 7.0 | 0.0 | 6.0 | 0.0 | 0.0 | 0.0 | 0.0 |
| 17 | 6.0 | 0.0 | 6.0 | 0.0 | 0.0 | 0.0 | 0.0 |
| 18 | 9.0 | 6.0 | 9.0 | 6.0 | 6.0 | 2.0 | 2.0 |
|  | 9.0 | 2.0 | 8.0 | 3.0 | 6.0 | 1.0 | 1.0 |
| 19 | 9.0 | 7.0 | 9.0 | 9.0 | 8.0 | 3.0 | 7.0 |
|  | 9.0 | 2.0 | 9.0 | 9.0 | 6.0 | 3.0 | 4.0 |
|  | 9.0 |  | 9.0 | 9.0 | 4.0 | 2.0 | 4.0 |
|  | 8.0 |  | 9.0 | 9.0 | 4.0 | 2.0 | — |

*THE RATINGS AVERAGED HAD A DISCREPANCY OF 6 OR GREATER, BETWEEN TWO OR MORE REPLICATES

In the foregoing, there has been provided a detailed description of particular embodiments of the present invention for the purpose of illustration and not limitation. It is to be understood that all other modifications, ramifications and equivalents obvious to those having skill in the art based on this disclosure are intended to be included within the scope of the invention as claimed.

I claim:

1. A compound having the structure:

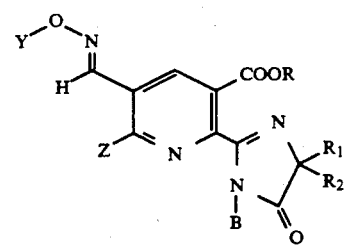

(I)

wherein
R is hydrogen,
C$_1$-C$_6$ alkyl optionally substituted with one of the following groups: C$_1$-C$_3$ alkoxy, halogen, phenyl or furyl, C₃-C₆ alkenyl optionally substituted with one of the following groups: C₁-C₃ alkoxy, halogen or phenyl, C₃-C₆ alkynyl, C₃-C₆ cycloalkyl optionally substituted with C₁-C₃ alkyl or a cation of an alkali metal, ammonium or organic ammonium;

R₁ is C₁-C₄ alkyl;

R₁ is C₁-C₄ alkyl or C₃-C₆ cycloalkyl, and when R₁ and R₂ are taken together with the carbon to Which they are attached, they may represent C₃-C₆ cycloalkyl;

B is hydrogen or COR₃, provided that when B is COR₃, R is other than hydrogen or a cation;

R₃ is C₁-C₄ alkyl or phenyl optionally substituted with one or two halogens, nitro or methoxy;

Y is hydrogen,

C₁-C₄ branched or unbranched alkyl optionally substituted with C₁-C₄ alkoxy, C₁-C₄ alkylthiol, halogen, CO₂R₄, CN, NHCOR₄, OCOR₄, furyl or a phenyl group optionally substituted with one or two halogens, C₁-C₂ alkyl or nitro, C₁-C₄ alkenyl optionally substituted with halogen, C₁-C₄ alkynyl, COR₄ or

CONHR₄;

Z is hydrogen or C₁-C₄ alkyl;

R₄ is C₁-C₄ alkyl;

an N-oxide thereof, when R is not alkenyl or alkynyl and Y is not alkenyl;

an optical isomer thereof, when R₁ and R₂ represent different substituents;

a tautomer thereof; or an acid-addition salt thereof, when R is other than a cation.

2. The compound according to claim 1, wherein R is hydrogen, C₁-C₆ alkyl or a cation of an alkali metal, ammonium or organic ammonium; R₁ is methyl; R₂ is isopropyl; B is hydrogen; Y is C₁-C₄ alkyl optionally substituted with C₁-C₄ alkoxy, C₁-C₄ alkylthio or phenyl; and Z is hydrogen or methyl; or the acid-addition salt thereof, when R is other than a cation.

3. The compound according to claim 2, wherein R is hydrogen or a cation of an alkali metal, ammonium or organic ammonium and Y is C₁-C₂ alkyl optionally substituted with C₁-C₄ alkoxy, C₁-C₄ alkylthio or phenyl; or the acid addition salt thereof, when R is hydrogen.

4. The compound according to claim 3, 5-formyl-2-(4-isopropyl-4-methyl-5-oxo-2-imidazolin-2-yl)-nicotinic acid, pyridine-5-(O-methyloxime) or an agronomically acceptable salt thereof.

5. The compound according to claim 3, 5-formyl-2-(4-isopropyl-4-methyl-5-oxo-2-imidazolin-2-yl)-nicotinic acid, pyridine-5-(O-ethyloxime) or an agronomically acceptable salt thereof.

6. The compound according to claim 3, methyl 5-formyl-2-(4-isopropyl-4-methyl-5-oxo-2-imidazolin-2-yl)nicotinate, pyridine-5-(O-methyloxime) or an agronomically acceptable salt thereof.

7. The compound according to claim 3, 5-formyl-2-(4-isopropyl-4-methyl-5-oxo-2-imidazolin-2-yl)-6-methyl-nicotinic acid, pyridine-5-(O-methyloxime) or an agronomically acceptable salt thereof.

8. The compound according to claim 3, 5-formyl-2-(4-isopropyl-4-methyl-5-oxo-2-imidazolin-2-yl)-nicotinic acid, pyridine-5-(O-benzyloxime) or an agronomically acceptable salt thereof.

9. A composition comprising an agronomically acceptable carrier and a herbicidally effective amount of a compound having the structure:

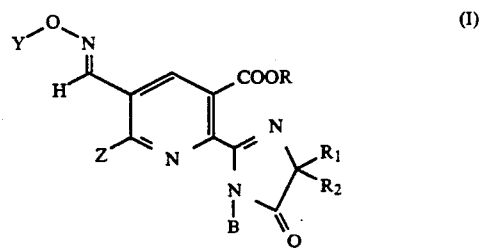

wherein

R is hydrogen,

C₁-C₆ alkyl optionally substituted with one of the following groups: C₁-C₃ alkoxy, halogen, phenyl or furyl, C₃-C₆ alkenyl optionally substituted with one of the following groups: C₁-C₃ alkoxy, halogen or phenyl, C₃-C₆ alkyl, C₃-C₆ cycloalkyl optionally substituted with C₁-C₃ alkyl or a cation of an alkali metal, ammonium or organic ammonium;

R₁ is C₁-C₄ alkyl;

R₂ is C₁-C₄ alkyl or C₃-C₆ cycloalkyl, and when R₁ and R₂ are taken together with the carbon to which they are attached, they may represent C₃-C₆ cycloalkyl;

B is hydrogen or COR₃, provided that when B is COR₃, R is other than hydrogen or a cation;

R₃ is C₁-C₄ alkyl or phenyl optionally substituted with one or two halogens, nitro or methoxy;

Y is hydrogen,

C₁-C₄ branched or unbranched alkyl optionally substituted with C₁-C₄ alkoxy, C₁-C₄ alkylthio halogen, CO₂R₄, CN, NHCOR₄, OCOR₄, furyl or a phenyl group optionally substituted with one or alkenyl optionally substituted with halogen, C₁-C₄ alkynyl, COR₄ or

CONHR₄;

Z is hydrogen or C₁-C₄ alkyl;

R₄ is C₁-C₄ alkyl;

an N-oxide thereof, when R is not alkenyl or alkynyl and Y is not alkenyl;

an optical isomer thereof, when R₁ and R₂ represent different substituents;

a tautomer thereof; or an acid-addition salt thereof, when R is other than a cation.

10. The composition according to claim 9, which contains the compound selected from the group consisting of 5-formyl-2-(4-isopropyl-4-methyl-5-oxo-2-imidazolin-2-yl)nicotinic acid, pyridine-5-(O-methyloxime); 5-formyl-2-(4-isopropyl-4-methyl-5-oxo-2-imidazolin-2-yl)-nicotinic acid, pyridine-5-(O-ethyloxime); methyl 5-formyl-2-(4-isopropyl-4-methyl-5-oxo-2-imidazolin-2-yl)-nicotinate, pyridine-5-(O-methyloxime); 5-formyl-2-(4-isopropyl-4-methyl-5-oxo-2-imidazolin-2-yl)-6-methyl-nicotinic acid, pyridine-5-(O- methyloxime); 5-formyl-2-(4-isopropyl-4-methyl-5-oxo-2-imidazolin-2-yl)-nicotinic acid, pyridine-5-(O-benzyloxime) and an agronomically acceptable salt thereof.

11. A method for the control of undesirable plant species comprising: applying to the foliage of said plants or to the soil or water containing seeds or other propagating organs thereof, a herbicidally effective amount of a compound having the structure:

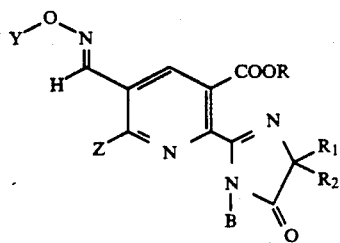

wherein
R is hydrogen,
$C_1$–$C_6$ alkyl optionally substituted with one of the following groups: $C_1$–$C_3$ alkoxy, halogen, phenyl or furyl,
$C_3$–$C_6$ alkenyl optionally substituted with one of the following groups: $C_1$–$C_3$ alkoxy, halogen or phenyl,
$C_3$–$C_6$ alkynyl,
$C_3$–$C_6$ cycloalkyl optionally substituted with $C_1$–$C_3$ alkyl or
a cation of an alkali metal, ammonium or organic ammonium;
$R_1$ is $C_1$–$C_4$ alkyl;
$R_2$ is $C_1$–$C_4$ alkyl or $C_3$–$C_6$ cycloalkyl, and when $R_1$ and $R_2$ are taken together With the carbon to which they are attached, they may represent $C_3$–$C_6$ cycloalkyl;
B is hydrogen or $COR_3$, provided that when B is $COR_3$, R is other than hydrogen or a cation;
$R_3$ is $C_1$–$C_4$ alkyl or phenyl optionally substituted with one or two halogens, nitro or methoxy;
Y is hydrogen,
$C_1$–$C_4$ branched or unbranched alkyl optionally substituted with $C_1$–$C_4$ alkoxy, $C_1$–$C_4$ alkylthiol, halogen, $CO_2R_4$, CN, $NHCOR_4$, $OCOR_4$, furyl or a phenyl group optionally substituted with one or two halogens, $C_1$–$C_2$ alkyl or nitro,
$C_1$–$C_4$ alkenyl optionally substituted with halogen,
$C_1$–$C_4$ alkynyl,
$COR_4$ or
$CONHR_4$;
Z is hydrogen or $C_1$–$C_4$ alkyl;
$R_4$ is $C_1$–$C_4$ alkyl;
an N-oxide thereof, when R is not alkenyl or alkynyl and Y is not alkenyl;
an optical isomer thereof, when $R_1$ and $R_2$ represent different substituents;
a tautomer thereof; or
an acid-addition salt thereof, when R is other than a cation.

12. The method according to claim 11, which comprises applying said compound to the foliage of said plants at a rate of about 0.012 kg per hectare to about 0.250 kg per hectare.

13. The method according to claim 11, which comprises applying said compound to the soil or water containing seeds or other propagating organs of said plants at a rate of about 0.012 kg per hectare to about 0.250 kg per hectare.

14. The method according to claim 11, which comprises applying the compound selected from the group consisting of 5-formyl-2-(4-isopropyl-4-methyl-5-oxo-2-imidazolin-2-yl)-nicotinic acid, pyridine-5-(O-methyloxime); 5-formyl-2-(4-isopropyl-4-methyl-5-oxo-2-imidazolin-2-yl)nicotinic acid, pyridine-5-(O-ethyloxime); methyl 5-formyl-2(4-isopropyl-4-methyl-5-oxo-2-imidazolin-2-yl)-nicotinate, pyridine-5-(O-methyloxime); 5-formyl-2-(4-isopropyl-4-methyl5-oxo-2-imidazolin-2-yl)-6-methyl-nicotinic acid, pyridine-5(O-methyloxime); 5-formyl-2-(4-isopropyl-4-methyl-5-oxo-2-imidazolin-2-yl)-nicotinic acid, pyridine-5-(O-benzyloxime) and an agronomically acceptable salt thereof.

* * * * *